United States Patent
Yamoto et al.

(10) Patent No.: US 10,052,973 B2
(45) Date of Patent: Aug. 21, 2018

(54) OCCUPANT DETECTION DEVICE USING ELECTROSTATIC SENSOR

(71) Applicant: MAZDA MOTOR CORPORATION, Hiroshima (JP)

(72) Inventors: Mitsuhiro Yamoto, Higashihiroshima (JP); Kiyonobu Takahashi, Hatsukaichi (JP); Masanobu Kosaka, Kure (JP); Kengo Iwata, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 0 days.

(21) Appl. No.: 15/397,157

(22) Filed: Jan. 3, 2017

(65) Prior Publication Data

US 2017/0210245 A1   Jul. 27, 2017

(30) Foreign Application Priority Data

Jan. 26, 2016   (JP) ................................ 2016-012277

(51) Int. Cl.
*G06F 7/00* (2006.01)
*B60N 2/00* (2006.01)
*G01N 27/22* (2006.01)

(52) U.S. Cl.
CPC ........... *B60N 2/002* (2013.01); *G01N 27/228* (2013.01)

(58) Field of Classification Search
CPC  B60N 2/002; G01N 27/228; B60R 21/01532; G01R 27/2605; G01V 3/08
USPC ........................ 701/36; 324/679, 457; 29/825
See application file for complete search history.

(56) References Cited

U.S. PATENT DOCUMENTS

| | | | | |
|---|---|---|---|---|
| 2008/0080741 A1* | 4/2008 | Yokoo | ................... | B60W 40/09 |
| | | | | 382/104 |
| 2012/0161777 A1* | 6/2012 | Nakagawa | ............. | B60N 2/002 |
| | | | | 324/457 |
| 2012/0299605 A1* | 11/2012 | Wakabayashi | ....... | H03K 17/955 |
| | | | | 324/679 |
| 2013/0234736 A1* | 9/2013 | Ootaka | .............. | G01R 27/2605 |
| | | | | 324/679 |
| 2014/0285223 A1* | 9/2014 | Inoue | ..................... | B60N 2/002 |
| | | | | 324/688 |

(Continued)

FOREIGN PATENT DOCUMENTS

JP        2013-186036 A       9/2013

*Primary Examiner* — Shardul D Patel
(74) *Attorney, Agent, or Firm* — Studebaker & Brackett PC

(57) ABSTRACT

The object is to provide an occupant detection device that can accurately detect whether there is a passenger, even when a personal computer, a tablet terminal, a smartphone or the like is placed on a vehicle seat. The occupant detection device is provided for a vehicle including a vehicle body, a vehicle seat and an in-vehicle battery. The occupant detection device includes: an electrostatic sensor provided in the seat and configured to measure capacitance between the sensor and the vehicle body; an interrupting unit configured to interrupt a function of the in-vehicle battery; a controller configured to temporarily activate the interrupting unit when a measured value of the electrostatic sensor is higher than a predetermined threshold; and a judgement unit configured to judge that there is a passenger when the measured value of the electrostatic sensor is higher than the predetermined threshold even while the interrupting unit is activated.

6 Claims, 3 Drawing Sheets

(56) References Cited

U.S. PATENT DOCUMENTS

2014/0335902 A1\* 11/2014 Guba .................... H04W 4/027
                                                                   455/456.4
2015/0224952 A1\* 8/2015 Ootaka ............. B60R 21/01532
                                                                   324/663

\* cited by examiner

OCCUPANT DETECTION DEVICE USING ELECTROSTATIC SENSOR

TECHNICAL FIELD

The present invention relates to an occupant detection device configured to detect whether or not there is a passenger in a vehicle by means of an electrostatic sensor.

BACKGROUND ART

The principle of an occupant detection device configured to detect whether or not there is a passenger in a vehicle by means of an electrostatic sensor (a capacitance sensor) is explained with reference to FIG. 3. As shown in FIG. 3, an electrostatic sensor 51 that measures capacitance between the electrostatic sensor 51 and a vehicle body 52 is buried in a vehicle seat 53. If a passenger sits on the vehicle seat 53, the capacitance between the electrostatic sensor 51 and the vehicle body 52 is increased, depending on relative dielectric constant of the passenger (human being), compared with the case wherein no passenger sits on the vehicle seat 53. Based on this principle, it is possible to judge whether or not there is a passenger on the vehicle seat 53.

JP-A-2013-186036 has proposed an occupant detection device for a vehicle, which uses the above principle and which achieves accurate detection at low cost even when some liquid is poured (applied) on the vehicle seat or some moisture is absorbed by the vehicle seat. The occupant detection device can achieve the accurate detection by changing the criterion of judgment by taking into account the humidity of environment.

The result of the detection (judgment) is used for another judgment, such as whether an air bag should be activated at a collision accident, or whether a warning about fastening of the seat belt should be issued.

PATENT DOCUMENT LIST

1. JP-A-2013-186036

SUMMARY OF INVENTION

Technical Problem

As shown in FIG. 4, when a personal computer is placed on the vehicle seat 53 for its battery charge by means of an in-vehicle battery, the personal computer is connected to the ground potential (GND) via a wire for the battery charge. Under the circumstance, capacitance between the electrostatic sensor 51 and the wire for the battery charge is measured, rather than the capacitance between the electrostatic sensor 51 and the vehicle body 52, so that the measured value is made greater. This means that misjudgment may occur, i.e., it may be judged that there is a passenger even when there is in fact no passenger.

In a similar manner, when a tablet terminal or smartphone is placed on the vehicle seat 53 for its connection to an in-vehicle USB terminal, due to the existence of the ground potential (GND) in USB wires, capacitance between the electrostatic sensor 51 and the USB wire is measured, rather than the capacitance between the electrostatic sensor 51 and the vehicle body 52, so that the measured value is made greater. This means that misjudgment may occur, i.e., it may be judged that there is a passenger even when there is in fact no passenger.

The present invention was made based on the above background. The object of the present invention is to provide an occupant detection device that can accurately detect whether there is a passenger, even when a personal computer, a tablet terminal, a smartphone or the like is placed on the vehicle seat 53.

Solution to Problem

The present invention is an occupant detection device provided for a vehicle, the vehicle including a vehicle body, a vehicle seat and an in-vehicle battery, the occupant detection device comprising: an electrostatic sensor provided in the seat and configured to measure capacitance between the electrostatic sensor and the vehicle body; an interrupting unit configured to interrupt a function of the in-vehicle battery; a controller configured to temporarily activate the interrupting unit when a measured value of the electrostatic sensor is higher than a predetermined threshold; and a judgement unit configured to judge that there is a passenger when the measured value of the electrostatic sensor is still higher than the predetermined threshold even while the interrupting unit is activated.

According to the present invention, when a measured value of the electrostatic sensor is higher than a predetermined threshold (which is assumed to be a case wherein a passenger sits on the vehicle seat or another case wherein an GND wire is placed on the vehicle seat), the controller temporarily activates the interrupting unit to interrupt the function of the in-vehicle battery, so that effects of the GND wire on the vehicle seat can be temporarily removed, if any. Subsequently, the judgement unit judges that there is a passenger only when the measured value of the electrostatic sensor is still higher than the predetermined threshold even while the interrupting unit is activated. Accordingly, it is possible to accurately detect whether or not there is a passenger.

For example, the in-vehicle battery may be a battery configured to be connected via an USB unit having an USB terminal. In this case, it is preferable that the interrupting unit is configured to interrupt the function of the in-vehicle battery by interrupting a wire in the USB unit.

Alternatively, for example, the in-vehicle battery may be a battery configured to be connected via both an USB unit having an USB terminal and an audio controlling unit. In this case, it is preferable that the interrupting unit is configured to interrupt the function of the in-vehicle battery by interrupting a wire in the audio controlling unit. Alternatively, in this case, it is preferable that the interrupting unit is configured to interrupt the function of the in-vehicle battery by interrupting a wire between the USB unit and the audio controlling unit.

Advantageous Effects of Invention

According to the present invention, when a measured value of the electrostatic sensor is higher than a predetermined threshold (which is assumed to be a case wherein a passenger sits on the vehicle seat or another case wherein an GND wire is placed on the vehicle seat), the controller temporarily activates the interrupting unit to interrupt the function of the in-vehicle battery, so that effects of the GND wire on the vehicle seat can be temporarily removed, if any. Subsequently, the judgement unit judges that there is a passenger only when the measured value of the electrostatic sensor is still higher than the predetermined threshold even while the interrupting unit is activated. Accordingly, it is possible to accurately detect whether or not there is a passenger.

DESCRIPTION OF EMBODIMENTS

Hereinafter, with respect to the attached figures, an embodiment of the present invention is explained.

Figure 1:
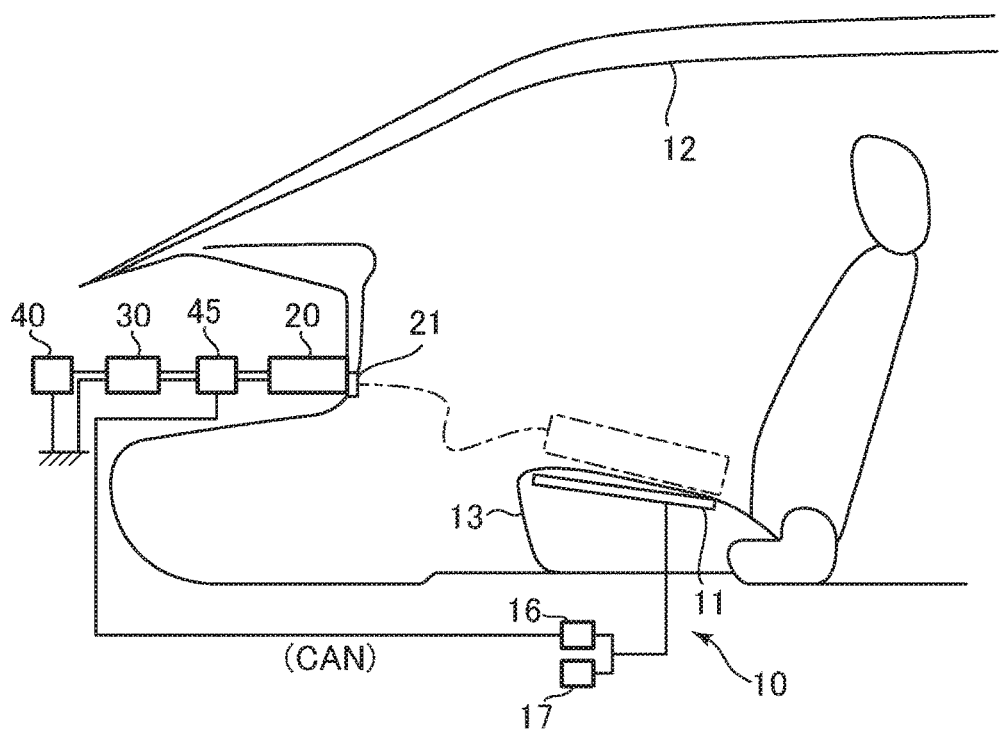
FIG. 1 is a schematic view showing an occupant detection device according to an embodiment of the invention.

FIG. 1 shows a vehicle interior of a car, in which an occupant detection device 10 according to an embodiment of the present invention is provided. In the embodiment shown in FIG. 1, an USB unit 20 having an USB terminal 21 is provided at a front area of the vehicle interior. The USB unit 20 is connected to an audio control unit 30. The audio control unit 30 is also called a tuner amplifier unit (TAU).

An in-vehicle battery 40 is available through the audio control unit 30 and the USB unit 20, for electric charge of a personal computer or a smartphone via the USB terminal 21. On the other hand, an interrupting unit 45 is configured to interrupt a function of the in-vehicle battery 40. In the present embodiment, the interrupting unit 45 is configured to interrupt (shutoff) a wire between the USB unit 20 and the audio control unit 30.

As shown in FIG. 1, in general, the vehicle seat 13 has a main seat on which a passenger can sit, and a backrest on which the passenger can settle back. The electrostatic sensor 11 is provided (buried) inside the seat 13 in order to measure capacitance between the electrostatic sensor 11 and the vehicle body 12. Specifically, the electrostatic sensor 11 is arranged between a seat cover for the main seat and a seat cushion of the main seat.

Various types of known electrostatic sensors are useable as the electrostatic sensor 11. For example, the electrostatic sensor 11 has a main electrode having a substantially flat shape for measuring capacitance between itself and the vehicle body 12, and a sensor circuit. In this case, it is preferable to provide a guard electrode below the main electrode, in order to generate electric flux only above the main electrode, i.e., only on the side of the passenger.

In addition, in the present embodiment, a controller 16 is configured to temporarily activate the interrupting unit 45 when a measured value of the electrostatic sensor 11 is higher than a predetermined threshold. The predetermined threshold corresponds to a value for judging that there is an adult passenger. The controller 16 and the interrupting unit 45 can be connected via a controller area network (CAN).

Furthermore, in the present embodiment, a judgement unit 17 is configured to judge that there is a passenger when the measured value of the electrostatic sensor 11 is still higher than the predetermined threshold even while the interrupting unit 45 is activated.

Next, an operation of the occupant detection device of the present embodiment is explained.

When the electrostatic sensor 11 detects a value higher than the predetermined threshold, there is a possibility that it should be judged that there is an adult passenger. However, in the present embodiment, such a judgment is not immediately made, but the controller 16 temporarily activates the interrupting unit 45 to interrupt (shutoff) the function of the in-vehicle battery 40 via the USB terminal 21. That is to say, since the GND wire on the vehicle seat 13 may have effects, if any, (possibility of) such effects are temporarily removed.

Subsequently, the judgement unit 17 judges that there is a passenger when the measured value of the electrostatic sensor 11 is still higher than the predetermined threshold even while the interrupting unit 45 is activated.

According to the present embodiment, by following the above steps, it is possible to accurately detect whether or not there is a passenger.

Figure 2:
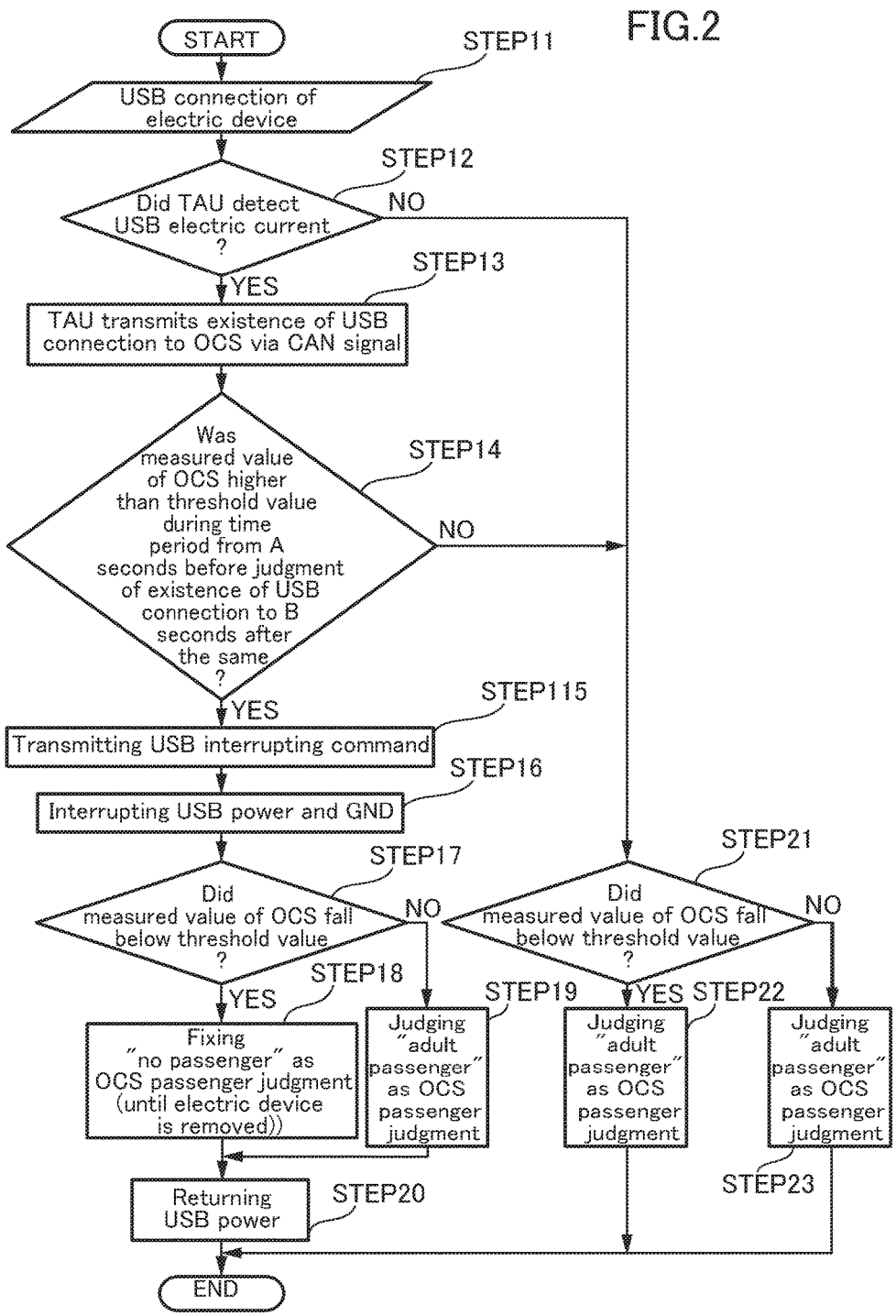
FIG. 2 is a schematic flowchart showing an example of operation of the occupant detection device shown in FIG. 1.
Figure 3:
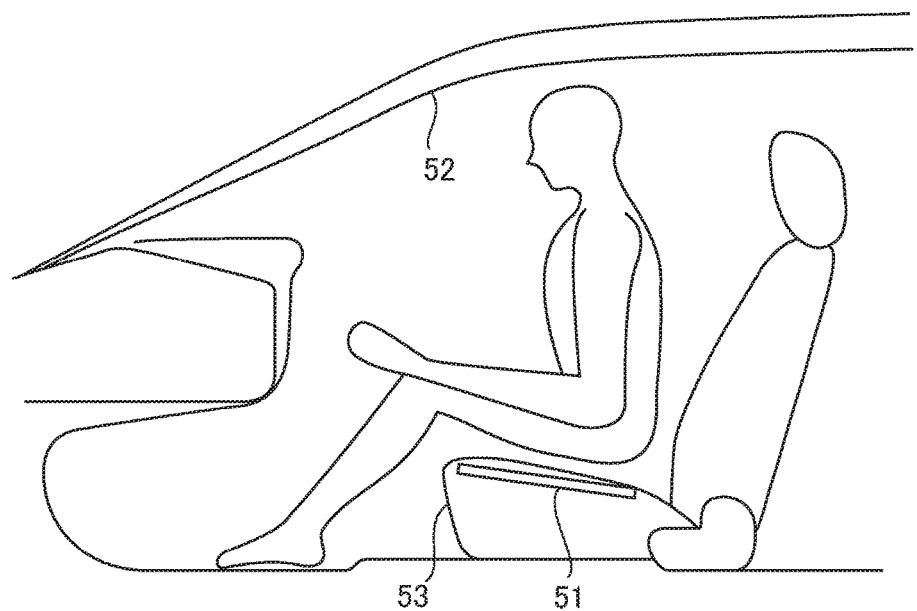
FIG. 3 is a schematic view showing a principle of an occupant detection device configured to detect whether or not there is a passenger using a capacitance sensor.
Figure 4:
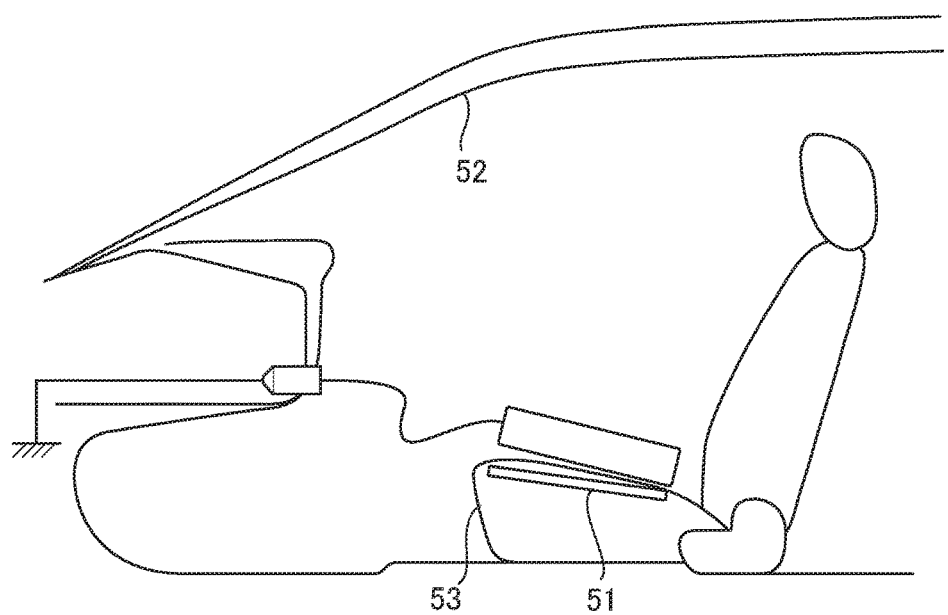
FIG. 4 is a schematic view showing a state wherein a personal computer is placed on a vehicle seat for its battery charge.

A more practical example of operation is explained with reference to FIG. 2. In the example of FIG. 2, the audio control unit 30 is able to detect whether or not the in-vehicle battery 40 is used via the USB terminal 21.

In the above embodiment, the interrupting unit 45 is configured to interrupt (shutoff) the wire between the USB unit 20 and the audio control unit 30. However, the present invention is not limited thereto. The interrupting unit 45 may be configured to interrupt (shutoff) a wire in the USB unit 20 and/or a wire in the audio control unit 30.

As shown in FIG. 2, an electric device such as a personal computer or a smartphone is connected to the USB terminal 21 (STEP 11). Thereafter, the audio control unit 30 detects whether or not the in-vehicle battery 40 is used via the USB terminal 21 (STEP 12).

As a result of the STEP 12, if the in-vehicle battery 40 is not used via the USB terminal 21 (if no USB electric current is detected), the conventional routine is adopted. That is to say, based on the measured value of the electrostatic sensor 11 (OCS), it is directly judged whether or not there is an adult passenger (STEPs 21 to 23). For example, when the electrostatic sensor 11 (OCS) detects a value higher than the predetermined threshold, it is directly and immediately judged that there is an adult passenger.

As a result of the STEP 12, if the in-vehicle battery 40 is used via the USB terminal 21 (if some USB electric current is detected), this information is transmitted to the controller 16 by using the controller area network (CAN), so that the controller 16 becomes standby state (STEP 13). Subsequently, it is judged whether or not the electrostatic sensor 11 detected a value higher than the predetermined threshold during a time period from A seconds (for example, 10 seconds) before the judgment of the STEP 12 to B seconds (for example, 10 seconds) after the same.

If the electrostatic sensor 11 did not detect a value higher than the predetermined threshold during the time period, it can be said that the effects by the usage of the in-vehicle battery 40 are small. Accordingly, the conventional routine is adopted. That is to say, subsequently, based on the measured value of the electrostatic sensor 11 (OCS), it is directly judged whether or not there is an adult passenger (STEPs 21 to 23). For example, when the electrostatic sensor 11 (OCS) detects a value higher than the predetermined threshold, it is directly and immediately judged that there is an adult passenger.

If the electrostatic sensor 11 detected a value higher than the predetermined threshold during the time period, it can be said that the effects by the usage of the in-vehicle battery 40 are large. In this case, the controller 16 temporarily activates the interrupting unit 45 to interrupt (shutoff) the function of the in-vehicle battery 40 via the USB terminal 21 (STEPs 15 to 16).

Subsequently, it is judged whether or not the measured value of the electrostatic sensor 11 (OCS) is still higher than the predetermined threshold while the interrupting unit 45 is activated (STEP 17). When the measured value of the electrostatic sensor 11 is still higher, the judgement unit 17 judges that there is a passenger (STEP 18). When the measured value of the electrostatic sensor 11 falls below the predetermined threshold while the interrupting unit 45 is activated, the judgement unit 17 judges that there is no passenger, and the judgment result is maintained until the connection of the electric device is removed (until the detection of the USB electric current is stopped) (STEP 19).

Subsequently, the temporal operation of the interrupting unit 45 is ended, and the function of the in-vehicle battery 40 is revived (STEP 20).

According to the above example of operation, only when there are the effects of the GND wire on the vehicle seat 13, the effects are temporarily removed, and then it is judged whether or not there is a passenger. Thus, it is possible to accurately and efficiently detect whether or not there is a passenger.

What is claimed is:

1. An occupant detection device provided for a vehicle, the vehicle including a vehicle body, a vehicle seat, an in-vehicle USB terminal and an in-vehicle battery, the occupant detection device comprising:
   an electrostatic sensor provided in the seat and configured to measure capacitance between the electrostatic sensor and the vehicle body;
   an interrupting unit configured to interrupt a power supply from the in-vehicle battery to the in-vehicle USB terminal;
   a controller configured to temporarily activate the interrupting unit when a measured value of the electrostatic sensor is higher than a predetermined threshold; and
   a judgement unit configured to judge that there is a passenger when the measured value of the electrostatic sensor is still higher than the predetermined threshold even while the interrupting unit is activated.

2. The occupant detection device according to claim 1, wherein
   the in-vehicle battery is a battery configured to be connected via an USB unit having the in-vehicle USB terminal.

3. The occupant detection device according to claim 2, wherein
   the interrupting unit is configured to interrupt the function of the in-vehicle battery by interrupting a wire in the USB unit.

4. The occupant detection device according to claim 1, wherein
   the in-vehicle battery is a battery configured to be connected via both an USB unit having the in-vehicle USB terminal and an audio controlling unit.

5. The occupant detection device according to claim 4, wherein
   the interrupting unit is configured to interrupt the function of the in-vehicle battery by interrupting a wire in the audio controlling unit.

6. The occupant detection device according to claim 4, wherein
   the interrupting unit is configured to interrupt the function of the in-vehicle battery by interrupting a wire between the USB unit and the audio controlling unit.

* * * * *